US006862917B2

United States Patent
Apostolos et al.

(10) Patent No.: US 6,862,917 B2
(45) Date of Patent: Mar. 8, 2005

(54) APPARATUS FOR DETECTING CHEMICAL AGENTS INCLUDING OLFACTORY INTERFEROMETRIC LENS AND METHOD OF USE

(75) Inventors: John T. Apostolos, Merrimack, NH (US); Leonard E. Russo, Nashua, NH (US)

(73) Assignee: Bae Systems Information and Electronic Systems Integration Inc., Nashua, NH (US)

( * ) Notice: Subject to any disclaimer, the term of this patent is extended or adjusted under 35 U.S.C. 154(b) by 0 days.

(21) Appl. No.: 10/260,317

(22) Filed: Sep. 30, 2002

(65) Prior Publication Data

US 2005/0028578 A1 Feb. 10, 2005

(51) Int. Cl.[7] .............................................. G01N 29/00
(52) U.S. Cl. ........................ 73/24.06; 73/23.34; 73/632
(58) Field of Search ............................ 73/24.01, 24.06, 73/23.34, 592, 632

(56) References Cited

U.S. PATENT DOCUMENTS

| | | | | | |
|---|---|---|---|---|---|
| 2,536,025 | A | * | 1/1951 | Blackburn ................... | 177/351 |
| 4,111,036 | A | * | 9/1978 | Frechette et al. ............. | 73/23.2 |
| 4,312,228 | A | | 1/1982 | Wohltjen ...................... | 73/597 |
| 5,129,262 | A | | 7/1992 | White et al. .................. | 73/599 |
| 5,323,636 | A | * | 6/1994 | McGowan et al. ......... | 73/24.01 |
| 5,339,675 | A | * | 8/1994 | DiLeo et al. ............... | 73/24.04 |
| 5,365,770 | A | * | 11/1994 | Meitzler et al. ............. | 73/24.06 |
| 5,589,396 | A | | 12/1996 | Frye et al. ...................... | 436/73 |
| 5,801,297 | A | * | 9/1998 | Mifsud et al. ............. | 73/23.34 |
| 5,959,191 | A | * | 9/1999 | Lewis et al. ................ | 73/31.05 |
| 6,212,938 | B1 | * | 4/2001 | Staples ........................ | 73/23.36 |
| 6,234,006 | B1 | * | 5/2001 | Sunshine et al. ........... | 73/29.01 |
| 6,237,397 | B1 | | 5/2001 | Shinar et al. ............... | 73/24.06 |
| 6,244,096 | B1 | * | 6/2001 | Lewis et al. .................. | 73/23.2 |
| 6,339,954 | B1 | * | 1/2002 | Naganawa et al. ......... | 73/61.79 |
| 6,360,584 | B1 | * | 3/2002 | Okubo et al. .............. | 73/23.34 |
| 6,378,370 | B1 | * | 4/2002 | Haskell et al. ................. | 73/579 |
| 6,405,135 | B1 | | 6/2002 | Adriany et al. ................. | 702/5 |
| 6,432,362 | B1 | * | 8/2002 | Shinar et al. ............. | 422/82.01 |
| 6,436,346 | B1 | * | 8/2002 | Doktycz et al. .............. | 422/51 |
| 6,467,332 | B1 | * | 10/2002 | Bertschi et al. ............. | 73/23.34 |
| 6,494,077 | B2 | * | 12/2002 | Aoyama et al. ........... | 73/23.34 |
| 6,575,013 | B2 | * | 6/2003 | Bao et al. ................... | 73/23.34 |

* cited by examiner

Primary Examiner—Daniel S. Larkin
(74) Attorney, Agent, or Firm—Daniel J. Long

(57) ABSTRACT

An apparatus and method for detecting gases, gasified agents or other analytes. The apparatus includes a solid body having a first surface area and a second surface area. A first, preferably polymeric, coating is superimposed on the first surface area of the solid body. A second, preferably polymeric, coating is superimposed on the second surface area of this solid body. The first coating and the second coating are different materials which adsorb different agents at different rates. A wave propagating transducer is positioned adjacent the solid body to propagate a first wavefront adjacent the first surface area of the solid body. This wave propagating transducer also propagates a second wavefront adjacent the second surface area of the solid body. These first and second wavefronts interfere to produce an interference pattern which is unique to the particular agent which is adsorbed by the first and second coatings. A transducer array records this interference pattern to identify the agent based on the nature of this interference pattern which will be uniquely characteristic of the agent.

29 Claims, 1 Drawing Sheet

US 6,862,917 B2

APPARATUS FOR DETECTING CHEMICAL AGENTS INCLUDING OLFACTORY INTERFEROMETRIC LENS AND METHOD OF USE

BACKGROUND OF THE INVENTION

1. Field of the Invention

The present invention relates to methods and apparatus for chemical analysis and more particularly to the analysis, detection, or identification of gases or gasified agents or, analytes based on their adsorption by other materials.

2. Brief Description of Prior Developments

The prior art discloses various methods and apparatus for analyzing gases or gasified agents or analytes based on their adsorption by different types of polymers.

In one such type of apparatus, an array of separate surface acoustic wave (SAW) devices, each coated with a polymer primarily sensitive to one analyte, is used to detect agents. The adsorption of agents causes a frequency shift dependent upon the polymer.

A disadvantage of this type of apparatus results from the use of separate arrays. Arrays are prone to drift owing to temperature or other environmental factors so that each array must be calibrated in a manner to be determined.

A need, therefore, exists for a method and apparatus which avoids these disadvantages.

SUMMARY OF INVENTION

The present invention is an apparatus for identifying or detecting the presence of gases, gasified agents or other analytes. For the purposes of this disclosure all such gases, gaseous agents and analytes will be collectively referred to as "agents". This apparatus includes a solid body having a first surface area and at least a second surface area. A first, preferably polymeric, coating is superimposed on the first surface area of the solid body. At least a second, preferably polymeric, coating is superimposed on the second surface area of this solid body. Additional surface areas and polymeric coatings may also be used. The first coating and the second coating are different materials which adsorb different gases at different rates. For example, the first coating may adsorb a first agent at a first rate and a second agent at a second rate, wherein these first and second rates are different from each other. The second coating may also adsorb the first agent at a third rate and the second agent at a fourth rate, wherein these third and fourth rates are different from each other. A wave propagating means is positioned adjacent the solid body to propagate an input wavefront adjacent input sides of first surface area and second areas of the solid body. On the output side of the first and second surface areas first and second wavefronts are produced. These first and second output wavefronts interfere to produce an interference pattern which is unique to the particular agent which is adsorbed by the first and second coatings. Additional output wavefronts will also be produced if additional surface areas and polymeric coatings are used, and these additional output wavefronts will interfere an be included in the interference pattern. An array of receiving means records this interference pattern to identify the agent based on the nature of this interference pattern which will be uniquely characteristic of the agent.

Also encompassed by the present invention is a method for identifying or detecting the presence of an agent. This method includes a first step of providing a solid body having a first surface area with a first coating and a second surface area with a second coating. The first coating and second coating are different materials that adsorb gases at different rates. The agent to be detected is caused to contact the first coating and second coating. The solid body is then excited so as to propagate an input wavefront adjacent the first surface area and the second wave front adjacent the second surface area and allowing the first and second wavefronts to produce an interference pattern. The agent is then identified based on this interference pattern which will be uniquely characteristic of the agent. Additional surface areas and coatings may be used to produce still more output wavefronts which will contribute to the interference pattern.

Also encompassed by the present invention is an olfactory interferometric lens. A plurality of different materials are superimposed on a solid substrate in side by side relation to form the olfactory interferometric lens. On one side of this lens there is a wave input side. A wavefront on the substrate enters the wave input side and exits from each material on the wave output side on the substrate to interfere and to produce an interference pattern which is characteristic of the agent adsorbed by the materials. Preferably, the materials are different polymeric coatings on the substrate.

BRIEF DESCRIPTION OF THE DRAWINGS

The present invention is further described with reference to the accompanying drawings in which.

DETAILED DESCRIPTION OF THE PREFERRED EMBODIMENT

Figure 1:
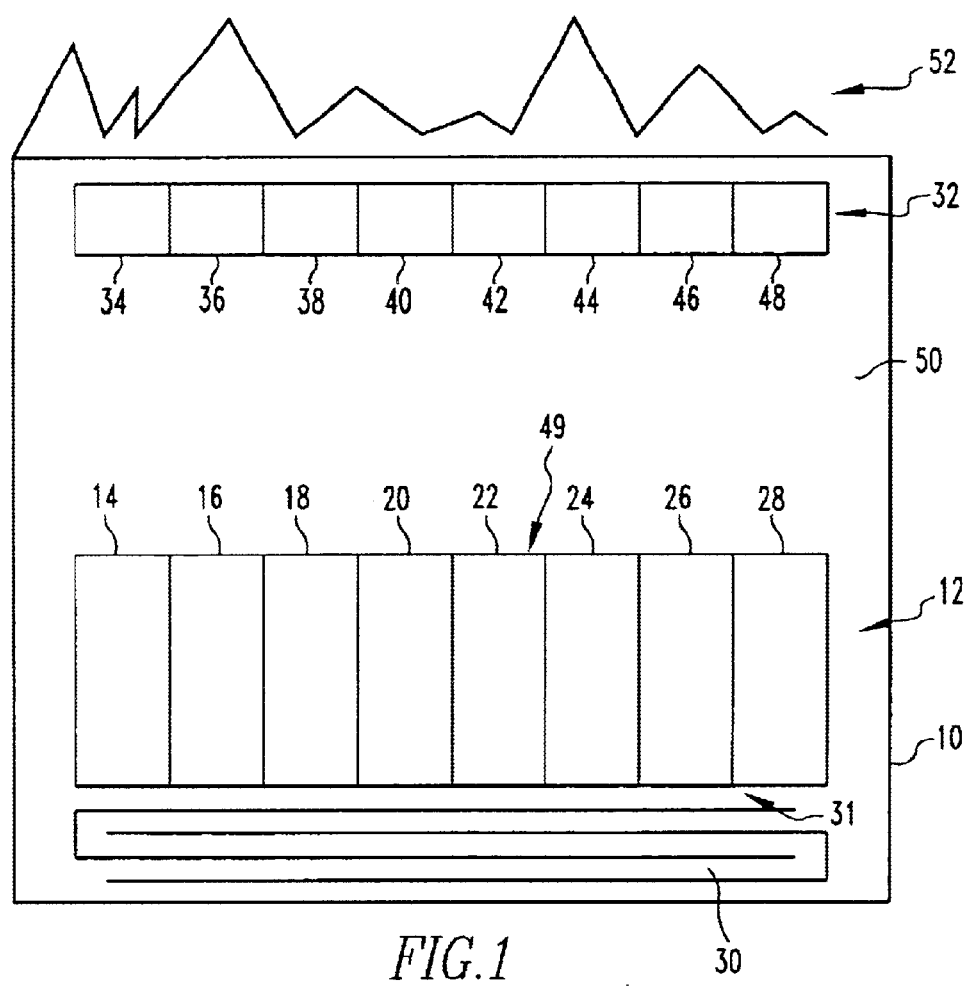
FIG. 1 is a schematic top plan view of a preferred embodiment of the apparatus of the present invention.

Referring to FIG. 1, the apparatus of the present invention includes a substrate 10 which is preferably metglass (metallic glass). Alternatively, the solid body substrate 10 may be quartz. Superimposed upon the substrate 10 there is a solid body olfactory interferometric polymer lens shown generally at 12. This polymer lens is comprised of a plurality of separate coatings 14, 16, 18, 20, 22, 24, 26, and 28 which are positioned in side-by-side arrangement separate surface areas on the substrate 10. Positioned behind the polymer lens 12 there is a single interdigital launching transducer 30 which is positioned in adjacent opposed relation to an input side 31 of the polymer lens 12. The transducer 30 produces an input wave which enters the polymer lens 12 at its input side 31. This transducer 30 spans all the components of the polymer lens 12. In opposed relation to the transducer 30 on the forward side of the solid body substrate 10 there is a transducer array shown generally at 32 which is comprised of transducers 34, 36, 38, 40, 42, 44, 46, and 48 which are positioned in adjacent opposed relation to an output side 49 of the polymer lens 12. While eight such transducers are shown, many more could be used, for example, there could be 64 or 128 such transducers. If the substrate 10 is metglass, it will have an upper layer of aluminum nitrate on which the transducers 34, 36, 38, 40, 42, 44, 46, and 48 will be deposited. Between the polymer lens 12 and the transducer array 32 there is a medial substrate 50. As is explained hereafter, an interference pattern 52 is produced as a result of the interaction of the wave fronts produced from each of the sections in the polymer lens 12.

The single transducer 30 spanning all the polymer coatings 14, 16, 18, 20, 22, 24, and 26 excites the polymer lens 12. Each polymer coating 14, 16, 18, 20, 22, 24, and 26 will distort the phase of the launched input wave in a specific manner depending upon the coating and the presence or absence of a particular agent. Thus, the complex wavefront produced will be altered by the agent. The output wavefronts exiting from output side 49 of the polymer lens 12 from the region of each polymer coating 14, 16, 18, 20, 22, 24, and 26 will propagate and interfere. A transducer array 32 records this interference pattern 52 which will be unique for each gaseous agent or analyte. The interference pattern 52, to first order, will shift across the array with changing temperature or environment; hence the pattern shape, detected by a correlator (not shown), will be preserved and the agent will be detected regardless of environmental factors.

Since there may be dispersion within the polymer lens 12, in a further preferred embodiment a slow chirp into the single digital transducer 30 will produce, over time, a two-dimensional interference pattern. Such a two-dimensional interference pattern will aid in the identification of the agent depending on the dispersiveness of the polymer-substrate combination. In other words, it is believed that there may be different behaviors at different frequencies. Those skilled in the art will appreciate that a resulting two dimensional array of data may allow for still detection capabilities.

In still another preferred embodiment, the substrate 10 may be configured in a roll or a spiral so that the surface area may be substantially increased for a given amount of space deviated to the apparatus as compared to the planar arrangement described above. It will be appreciated that such an increase in surface area may substantially increase the sensitivity of the apparatus. Those skilled in the art will also appreciate that it may be advantageous to use metglass (metallic glass) or some other flexible material for the substrate 10 in such a rolled or spiral embodiment.

Those skilled in the art will appreciate that the apparatus and method described above will be particularly useful as a low cost means for detecting the presence of one or more specific agents. Those skilled in the art will also appreciate that the specific polymers which we selected for use in the olfactory lens 12 may be selected based on the particular agent or agents for which any particular embodiment of this apparatus will be designed to detect or identify.

It will be appreciated that an apparatus and method has been described which allow for an accurate and cost effective analysis of agents based on their adsorption by different types of polymers or other materials and the production of an interference pattern which will be unique to such agents.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. An apparatus for detecting agents comprising:
   a solid body having a first surface area and a second surface area;
   a first coating superimposed on the first surface area of the solid body, and a second coating superimposed on the second surface area of the solid body, wherein said first coating and second coating are different materials;
   a wave propagating transducer adjacent the solid body to propagate an input wave front adjacent the first surface area of the solid body and the second surface area of the solid body and thereby result in a first output wavefront adjacent the first surface area of the solid body and a second output wavefront adjacent the second surface area of the solid body, wherein said first output wave front and said second output wave front interfere to produce an interference pattern; and
   a wave receiving transducer means for recording the interference pattern produced by said first output wave front and second output wave front;
   wherein the first coating and the second coating each adsorb different agents at different rates, and the first coating adsorbs a first agent at a first rate and a second agent at a second rate, and said first and second rates are different from each other, and the second coating adsorbs the first agent at a third rate and the second agent at a fourth rate, and said third and fourth rates are different from each other.

2. The apparatus of claim 1 wherein the first coating and the second coatings are both polymers.

3. The apparatus of claim 1 wherein the first agent produces a first interference pattern, the second agent produces a second interference pattern, and there is a third agent and the third agent produces a third interference pattern and the fourth agent produces a fourth interference pattern, and there is a fourth agent and said first, second, third, and fourth interference patterns are all different from each other.

4. The apparatus of claim 1 wherein the wave propagating transducer substantially spans the entire solid body.

5. The apparatus of claim 1 wherein the wave propagating transducer consists of a single transducer.

6. The apparatus of claim 1 wherein the wave receiving transducer means is a transducer array.

7. The apparatus of claim 6 wherein the transducer array substantially spans the entire solid body.

8. The apparatus of claim 1 wherein the solid body, the wave propagating transducer, and the wave receiving transducer array are all superimposed on a substrate.

9. The apparatus of claim 8 wherein the substrate is comprised of metallic glass.

10. The apparatus of claim 8 wherein the substrate is comprised of quartz.

11. The apparatus of claim 1 wherein there are at least eight different coatings on the solid body.

12. The apparatus of claim 1 wherein the solid body is an interferometric lens.

13. The apparatus of claim 1 wherein the solid body is an elongated element in which the first surface area, the second surface area and a plurality of additional surface areas are positioned in transverse side by side arrangement and said additional surface areas each have a coating which is comprised of a material which is different from the material of the coating of each of the other additional surface areas.

14. A method for detecting an agent to be identified comprising the steps of:
   providing a solid body having a first surface area having a first coating and a second surface area having a second coating, wherein said first coating and said second coating are different materials, wherein the first coating and the second coating each adsorb different agents at different rates, and the first coating adsorbs a first agent at a first rate and a second agent at a second rate and said first and second rates are different from each other, and the second coating adsorbs the first agent at a third rate and the second agent at a fourth rate and said first and second rates are different from each other;

causing said agent to be identified to contact said first coating and said second coating;

exciting the solid body with an input wave front energy source so as to propagate a first output wave front adjacent the first surface area and a second output wave front adjacent the second surface area and allowing said first wave front and said second wave front to produce an interference pattern; and identifying the agent to be identified based on said interference pattern.

15. The method of claim 14 wherein the first coating and the second coating are both polymers.

16. The method of claim 14 wherein the first coating and the second coating adsorb different agents at different rates.

17. The method of claim 16 wherein the solid body is an elongated element in which the first surface area, the second surface area and a plurality of additional surface areas are positioned in transverse side by side arrangement and said additional surface areas all have a coating which is comprised of a material which is different from the material of the coating of each of the other additional surface areas.

18. The method of claim 14 wherein the solid body is excited by a transducer.

19. The method of claim 14 wherein the first wave front and the second wave front are propagated on a substrate.

20. The method of claim 19 wherein the substrate is metallic glass.

21. The method of claim 19 wherein the substrate is quartz.

22. The method of claim 14 wherein the interference pattern is recorded by a wave receiving transducer array.

23. An olfactory interferometric lens for detecting an agent comprising:

a solid substrate;

a plurality of different materials which adsorb different agents at different rates and which are positioned in side by side relation on said solid substrate to form a wave input side and a wave output side, whereby upon excitation by an appropriate wavefront energy source placed at said wavefront input side, wavefronts exiting from said wave output side from each of said different materials on said solid substrate will interfere to product an interference pattern characteristic of the agent adsorbed by the materials.

24. The olfactory interferometric lens of claim 23 wherein the different materials comprise different polymeric coatings on the solid substrate.

25. The olfactory interferometric lens of claim 23 wherein the different materials comprise different polymeric coatings.

26. The olfactory interferometric lens of claim 25 wherein the solid substrate is metallic glass.

27. The olfactory interferometric lens of claim 25 wherein the solid substrate is quartz.

28. An apparatus for detecting agents comprising:

a metallic glass substrate;

a solid body having a first surface area and a second surface area and being superimposed on the metallic glass substrate;

a first coating superimposed on the first surface sea of the solid body, and a second coating superimposed on the second surface area of the solid body, wherein said first coating and second coating are different materials;

a wave propagating transducer superimposed on the metallic glass substrate adjacent the solid body to propagate an input wave front adjacent the first surface area of the solid body and the second surface area of the solid body and thereby result in a first output wavefront adjacent the first surface area of the solid body and a second output wavefront adjacent the second surface area of the solid body, wherein said first output wave front and said second output wave front interfere to produce an interference pattern; and a wave receiving transducer array superimposed on the metallic glass substrate for recording the interference pattern produced by said first output wave front and second output wave front.

29. An apparatus for detecting agents comprising:

an interferometric lens comprised of a solid body having a first surface area and a second surface area;

a first coating superimposed on the first surface area of the solid body, and a second coating superimposed on the second surface area of the solid body, wherein said first coating and second coating are different materials;

a wave propagating transducer adjacent the solid body to propagate an input wave front adjacent the first surface area of the solid body and the second surface area of the solid body and thereby result in a first output wavefront adjacent the first surface area of the solid body and a second output wavefront adjacent the second surface area of the solid body, wherein said first output wave front and said second output wave front interfere to produce an interference pattern; and a wave receiving transducer array for recording the interference pattern produced by said first output wave front and second output wave front.

* * * * *